(12) United States Patent
Narciso-Martinez et al.

(10) Patent No.: US 10,071,235 B1
(45) Date of Patent: Sep. 11, 2018

(54) SLIDE-BUTTON CATHETER CONNECTOR DEVICE

(71) Applicants: Luis Alberto Narciso-Martinez, Caracas (VE); Maura Spizzo-De Narciso, Caracas (VE)

(72) Inventors: Luis Alberto Narciso-Martinez, Caracas (VE); Maura Spizzo-De Narciso, Caracas (VE)

( * ) Notice: Subject to any disclaimer, the term of this patent is extended or adjusted under 35 U.S.C. 154(b) by 460 days.

(21) Appl. No.: 14/734,497

(22) Filed: Jun. 9, 2015

(51) Int. Cl.
*A61M 25/16* (2006.01)
*A61M 25/18* (2006.01)
*A61M 39/12* (2006.01)
*A61M 39/10* (2006.01)

(52) U.S. Cl.
CPC ........ *A61M 39/12* (2013.01); *A61M 39/1011* (2013.01)

(58) Field of Classification Search
CPC ...... A61M 39/02; A61M 39/10; A61M 39/12; A61M 39/1011; A61M 2005/3268
USPC ................................................ 604/533, 535
See application file for complete search history.

(56) References Cited

U.S. PATENT DOCUMENTS

| | | |
|---|---|---|
| 4,006,744 A | 2/1977 | Steer |
| 4,405,163 A | 9/1983 | Voges et al. |
| 4,792,163 A | 12/1988 | Kulle |
| 4,929,236 A | 5/1990 | Sampson |
| 5,368,573 A | 11/1994 | Andrew |
| 5,464,400 A | 11/1995 | Collins |
| 5,496,274 A | 3/1996 | Graves et al. |
| 6,350,260 B1 | 2/2002 | Goebel et al. |
| 7,044,936 B2 | 5/2006 | Harding et al. |
| 7,717,900 B2 | 5/2010 | di Palma |
| 8,142,417 B2 | 3/2012 | Pajunk et al. |
| 8,480,560 B2 | 7/2013 | Vendely |
| 8,647,300 B2 | 2/2014 | Kunzler et al. |
| 8,696,647 B2 | 4/2014 | Bizup et al. |
| 2005/0057042 A1* | 3/2005 | Wicks ................. F16L 37/0841 285/305 |
| 2012/0041426 A1 | 2/2012 | Bizup |

* cited by examiner

*Primary Examiner* — Edelmira Bosques
*Assistant Examiner* — Tiffany Legette-Thompson
(74) *Attorney, Agent, or Firm* — John Rizvi; Gold & Rizvi, P.A.

(57) ABSTRACT

A catheter connector device is provided including a device housing having a first port and a second port. A fixed sleeve support portion and a flexible, cantilevered sleeve cover extend longitudinally within a housing interior, to carry a flexible tubular sleeve having a sleeve through bore extending from the first port to the second port, for removable insertion of a catheter. The sleeve cover has a first portion, a second portion extending from the first portion and a third portion narrower than the first portion extending from the second portion. A slidable catheter lock switch, or slide button, is positional between a catheter-unlocking position adjacent to the third portion of the sleeve cover and a catheter-locking position engaging the first portion of the sleeve cover and flexing the tubular sleeve cover to crimp the tubular sleeve and retain the catheter within.

20 Claims, 5 Drawing Sheets

SLIDE-BUTTON CATHETER CONNECTOR DEVICE

FIELD OF THE INVENTION

The present invention relates generally to medical devices, and more particularly, to a slide-button operated catheter connector device which can facilitate quick and easy connection of a syringe or other fluid application and/or removal device to an epidural catheter inserted into the epidural space of a patient and protruding outwardly from the patient's body.

BACKGROUND OF THE INVENTION

Catheters are thin tubes commonly used in medicine for accurately administering or withdrawing fluids. Typically, one end of a catheter is inserted into a patient, and an opposite end is connected to a fluid application and/or removal device, such as a syringe, for appropriately administering or withdrawing fluids to or from a patient. A catheter is usually connected to a syringe via an interfacing catheter connector. Such catheter connectors enable a medical practitioner to accurately administer or drain fluids by operating the connected syringe. However, traditional catheter connectors have various problems.

For example, traditional catheter connectors are commonly composed of a single part cone shaped or cylindrical tube, in which a catheter is inserted into one end of the tube, and a syringe, is attached at an opposite end of the tube. Such traditional catheter connectors usually rely solely on material tension of the connector tube to secure a catheter, and thus can result in an insecure connection.

Further, some common traditional catheter connectors require assembling and/or configuring multiple external parts to properly connect a catheter to a syringe. For example, some common catheter connectors require inconvenient latching, clamping and/or attaching various external components, such as plastic flaps, clamps, hinges, etc. Most catheter connectors are manufactured to be cheap and space-efficient. As such, these external parts may easily break, or may be hard to operate in emergency situations.

Epidural catheter connectors are a specific type of catheter connector designed to interface between a fluid application and/or removal device and an epidural catheter inserted into the epidural space and protruding from the patient's body, generally for providing controlled and extremely precise administration of epidural anesthetics. An epidural catheter must tightly yet unobtrusively grip the catheter in order to prevent disconnection of the catheter (which can be harmful to the patient) and guarantee correct flow of the epidural anesthetic through the catheter. In addition, epidural catheter connectors should preferably be easy to attach to the catheter, minimizing the risk of errors and pulling of the catheter. Epidural catheter connectors known in the art, namely, catheter-clamping connectors and threaded connectors are in risk of obstructing the catheter and also require excessive manual operation of the connector in order to fasten onto the catheter.

Thus, there is an established need for an epidural catheter connector device that can easily and safely be attached to an epidural catheter in order to facilitate the further connection of a syringe or other fluid application and/or removal device to a catheter for delivery of medical fluids to or remove fluids from a patient.

SUMMARY OF THE INVENTION

The present invention is directed to a catheter connector device which facilitates quick and easy connection of a syringe or other fluid application and/or removal device to a catheter, and particularly to an epidural catheter generally for delivery of an epidural anesthetic to a patient. The catheter connector device includes a device housing having a first port for connection of a syringe or fluid application and/or removal device and a second port for the insertion of a catheter. A tubular sleeve extends between the first port and the second port in the housing interior of the device housing. A slidable catheter lock switch, or slide button, on the device housing can be moved to a catheter-unlocking position in which a catheter is locked in the tubular sleeve and a catheter-locking position in which the catheter is unlocked for insertion or removal in the tubular sleeve.

Introducing a first embodiment of the invention, the present invention consists of a catheter connector device for interfacing between a catheter and a fluid application and/or removal device, comprising a device housing, delimiting a housing interior therein. The device housing includes a first port and a second port comprising a respective first port opening and second port opening. The first and second port openings communicate an exterior of the catheter connector device with the housing interior. The device housing further comprises a sidewall having a slot. A fixed sleeve support portion extends within the housing. A cantilevered flexible sleeve cover extends from the device housing into the housing interior, the sleeve cover having a first portion extending from an inside surface of the device housing. The catheter connector device further includes a flexible tubular sleeve comprising a sleeve through bore. The tubular sleeve is arrangeable between the fixed sleeve support portion and the sleeve cover, with the sleeve through bore in fluid communication with the first and second port openings. In addition, the catheter connector device includes a user-operable catheter lock switch, which is slidable along the slot. The catheter connector device is configured to adopt, by selectively sliding the catheter lock switch in opposite directions, a catheter-locking configuration and a catheter-unlocking configuration. In the catheter-locking configuration, an inner surface of the catheter lock switch is slid onto the first portion of the sleeve cover and maintains the sleeve cover in a flexed position towards the fixed sleeve support portion, compressing the tubular sleeve for gripping a catheter inserted in the through bore of the tubular sleeve. In the catheter-unlocking configuration, instead, the inner surface of the catheter lock switch does not contact the first portion of the sleeve cover and the sleeve cover is biased away from the fixed sleeve support portion relaxing the compressing of the tubular sleeve.

In a second aspect, the sleeve cover can further include a second portion extending from the first portion towards a free end of the sleeve cover. The second portion is at a greater distance from the slot than the first portion, and at an increasing distance from the slot.

In another aspect, the second portion can be tapered.

In another aspect, the sleeve cover further comprises a third portion extending from the second portion towards the free end of the sleeve cover. The third portion is at a greater distance from the slot than the first and second portions.

In another aspect, in the catheter-unlocking configuration, the catheter lock switch can be arranged in registration with the third portion.

In another aspect, the first and second ports are arranged at opposite ends of the catheter connector device along a longitudinal direction. The first port opening, the sleeve bore and the second port opening can be aligned along the longitudinal direction.

In another aspect, the slot can be arranged in the longitudinal direction.

In another aspect, the device housing can include a first housing portion and a second housing portion fastened to one another. The fixed sleeve support portion can from an inner surface of the second housing portion into the inner space, and the sleeve cover can extend from an inner surface of the first housing portion.

In another aspect, the first port can be comprised in the first housing portion and the second port can be comprised in the second housing portion.

In another aspect, the fixed sleeve support portion can rest transversely on the first housing portion, preventing transverse movement of the fixed sleeve support portion when sliding the catheter lock switch onto the first portion to achieve the catheter-locking configuration.

In another aspect, the catheter connector device is reversibly and repeatedly alterable from the catheter-unlocking configuration to the catheter-locking configuration.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward an epidural catheter connector device which facilitates quick and easy connection of a syringe or other fluid application and/or removal device to an epidural catheter, generally for delivery of an epidural anesthetic to a patient.

Figure 1:
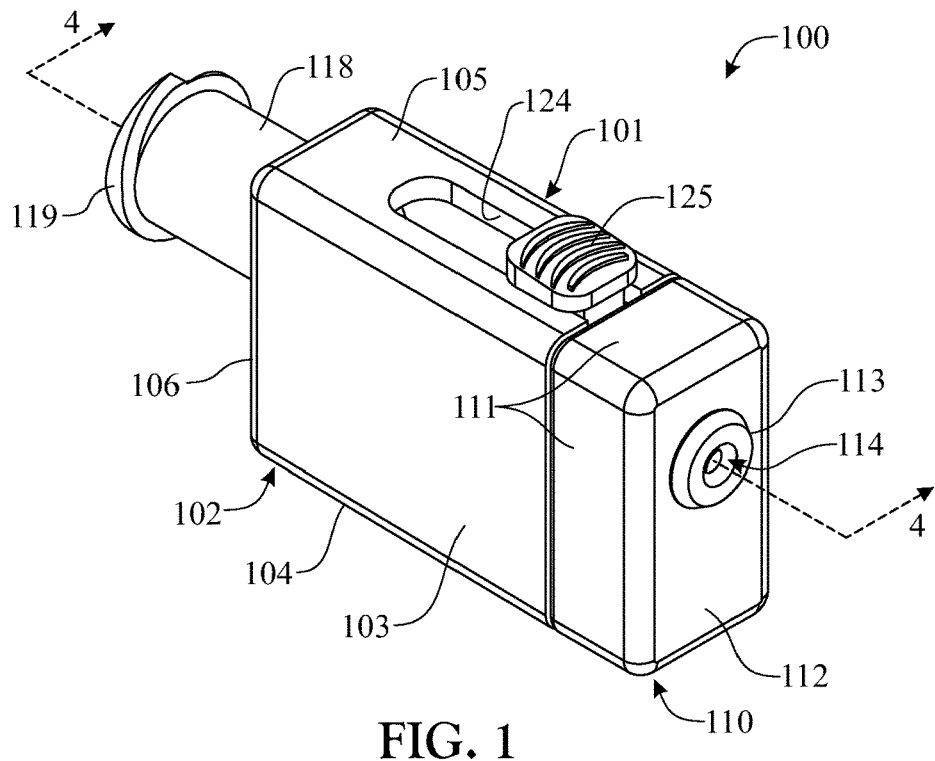
FIG. 1 is an isometric rear view of an exemplary embodiment of the catheter connector device of the present invention.
Figure 2:
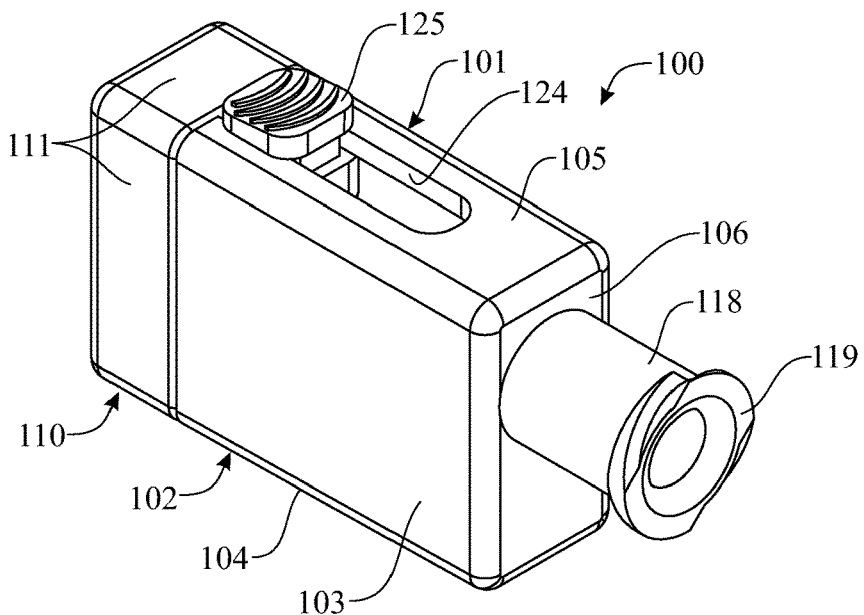
FIG. 2 is an isometric front view of the catheter connector device of FIG. 1.
Figure 3:
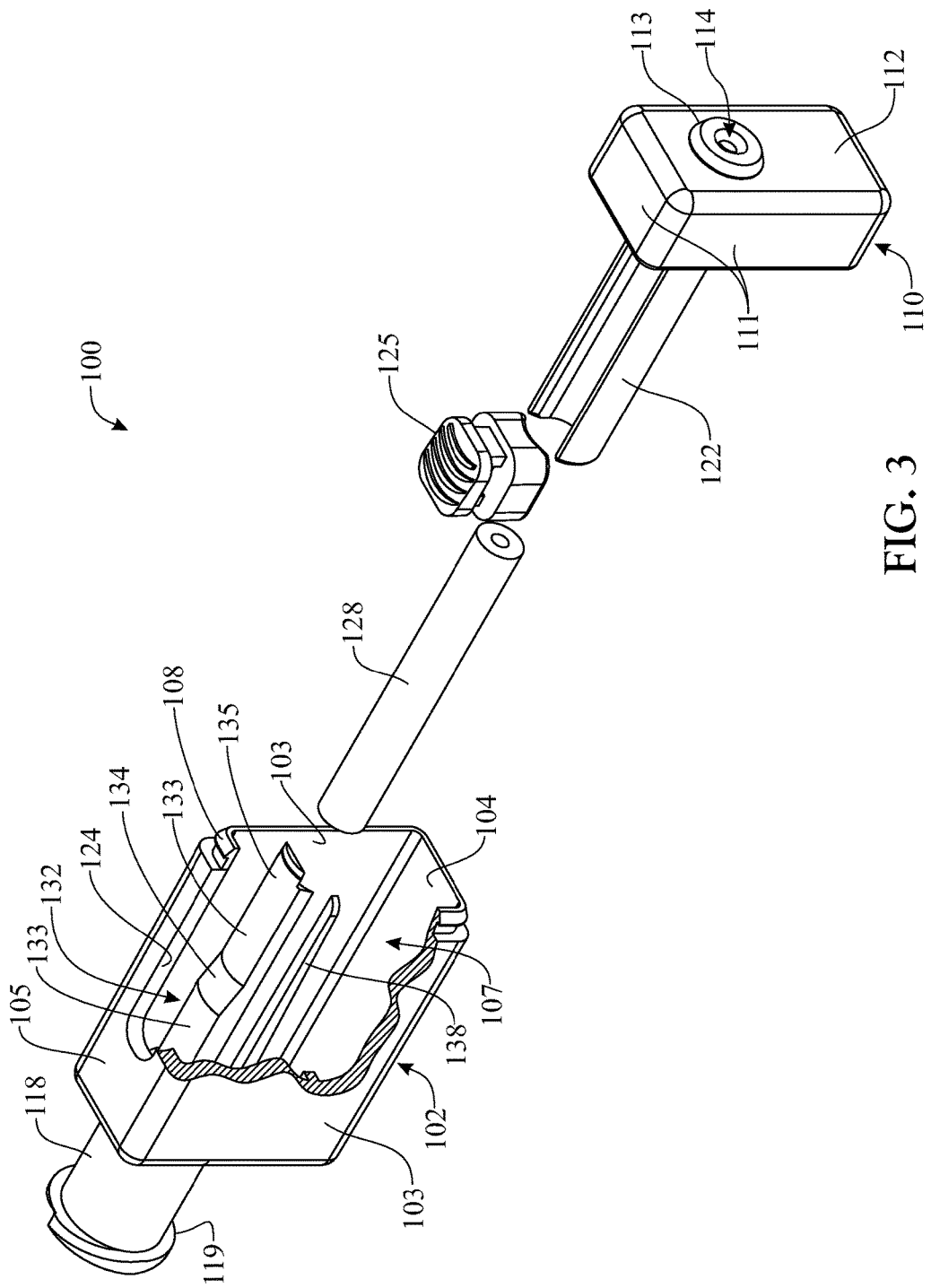
FIG. 3 is an isometric rear exploded view showing interior components of the catheter connector device of FIG. 1.
Figure 4:
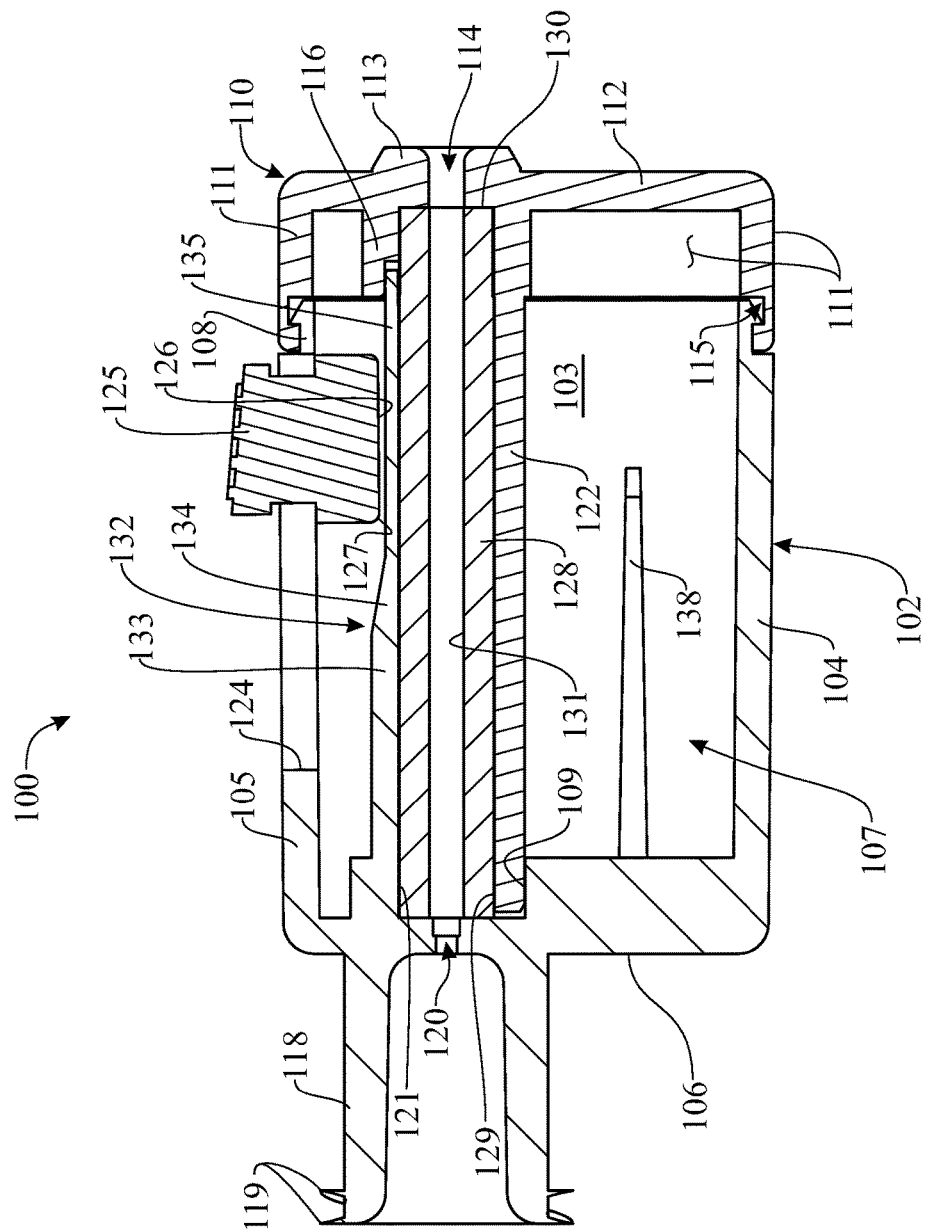
FIG. 4 is cross-sectional side elevation view, taken along sectional plane 14-4 indicated in FIG. 1, of the catheter connector device of FIG. 1.

Referring initially to FIGS. 1 through 3, a catheter connector device 100 is illustrated in accordance with an exemplary embodiment of the present invention. As shown, the catheter connector device 100 includes a device housing 101 which may be generally elongated and rectangular in some embodiments. The device housing 101 can be comprised of a first housing portion 102 and a second housing portion 110. The first housing portion 102 may include a pair of generally elongated, parallel, spaced-apart housing side walls 103, a housing bottom wall 104 and a housing top wall 105 extending between the housing side walls 103, and a first port wall 106 extending between the housing side walls 103, the housing bottom wall 104 and the housing top wall 105 at a first end of the first housing portion 102. As shown in FIG. 3, a housing flange 108 may extend from the housing side walls 103, the housing bottom wall 104 and the housing top wall 105 at a second end of the first housing portion 102 for purposes which will be hereinafter described. As illustrated in FIGS. 3 and 4, the first housing portion 102 has a housing interior 107. At least one sidewall reinforcing rib 138 may extend along an interior surface of at least one of the housing side walls 103 in the housing interior 107 for reinforcement purposes.

A first port 118 may protrude from the first port wall 106 of the first housing portion 102. The first port 118 may be fitted with first port threads 119 to facilitate connection of a syringe 144 (FIG. 5) to the first port 118 for purposes which will be hereinafter described. In some embodiments, the first port 118 and first port threads 119 may be formed as a conventional luer-lock connector. As shown in the cross-sectional view of FIG. 4, a first port opening 120 may extend through the first port wall 106 of the first housing portion 102. The first port opening 120 communicates with the first port 118. A sleeve cavity 121 may be provided in an interior surface of the first port wall 106.

As shown in FIGS. 1 through 3, a second housing portion 110 may be detachably attached to the housing flange 108 of the first housing portion 102. The second housing portion 110 may include multiple attachment side walls 111 and a second port wall 112 which extends between the attachment side walls 111. A housing flange groove 115, best shown in FIG. 4, may be provided in an interior surface of the attachment side walls 111. The housing flange groove 115 may be appropriately sized and configured to accommodate the housing flange 108 on the first housing portion 102 and detachably mount the second housing portion 110 to the first housing portion 102, the first housing portion 102 and the second housing portion 110 thus forming an enclosure. A second port 113 may be provided on an exterior surface of the second port wall 112; in the present embodiment the second port 113 protrudes outwardly from the exterior surface of the second port wall 112 to facilitate tactile retrieval of the second port 113. The second port 113 is in longitudinal opposition to the first port 118. A second port opening 114 may extend through the second port wall 112 and the second port 113 for purposes which will be hereinafter described. A cover anchoring wall 116 may protrude from an interior surface of the second port wall 112 for purposes which will be hereinafter described.

As particularly illustrated in FIGS. 3 and 4, an elongated fixed sleeve support portion 122 may extend from an interior surface of the second port wall 112 of the second housing portion 110 into the housing interior 107 of the first housing portion 102. A free end of the fixed sleeve support portion 122 can rest on a seating surface 109 of the first housing portion 102. The fixed sleeve support portion 122 may be disposed beneath the second port opening 114 of the second port 113 and may have a generally semicircular or crescent-shaped cross-section. The purpose of the fixed sleeve support portion 122 will be hereinafter described.

As further illustrated in FIGS. 3 and 4, a cantilevered elongated sleeve cover 132 may extend from an interior surface of the first port wall 106 of the first housing portion 102 into the housing interior 107. The sleeve cover 132 extends in a longitudinal direction and is slightly flexible, i.e. can be subject to bending in a transverse direction to and from the fixed sleeve support portion 122 for purposes that are hereinafter described. The sleeve cover 132 may have a generally semicircular or crescent-shaped cross-section. When the second housing portion 110 is attached to the first housing portion 102, the sleeve cover 132 is disposed above and in generally spaced-apart relationship to the fixed sleeve support portion 122. As shown, the sleeve cover 132 has various thicknesses along its length. Specifically, a first portion 133 extends from the first port wall 106, a second portion 134 extends from the first portion 133, and a third portion 135 extends from the second portion 134. The third portion 135 is narrower than the first portion 133 and may engage the cover anchoring wall 116 which protrudes from the interior surface of the second port wall 112 of the second housing portion 110.

An elongated tubular sleeve 128 may be seated in the fixed sleeve support portion 122 of the second housing portion 110. The tubular sleeve 128 may be fabricated of a flexible pharmaceutical-grade plastic or other material. As best shown in FIG. 4, a sleeve through bore 131 extends through the tubular sleeve 128. The sleeve cover 132 may extend over the upper portion of the tubular sleeve 128. Accordingly, the tubular sleeve 128 may have a first sleeve end 129 which is inserted in the sleeve cavity 121 and disposed in fluid communication with the first port opening 120 of the first port 118 and a second sleeve end 130 which engages the cover anchoring wall 116 and is disposed in fluid communication with the second port opening 114 of the second port 113.

Figure 6:
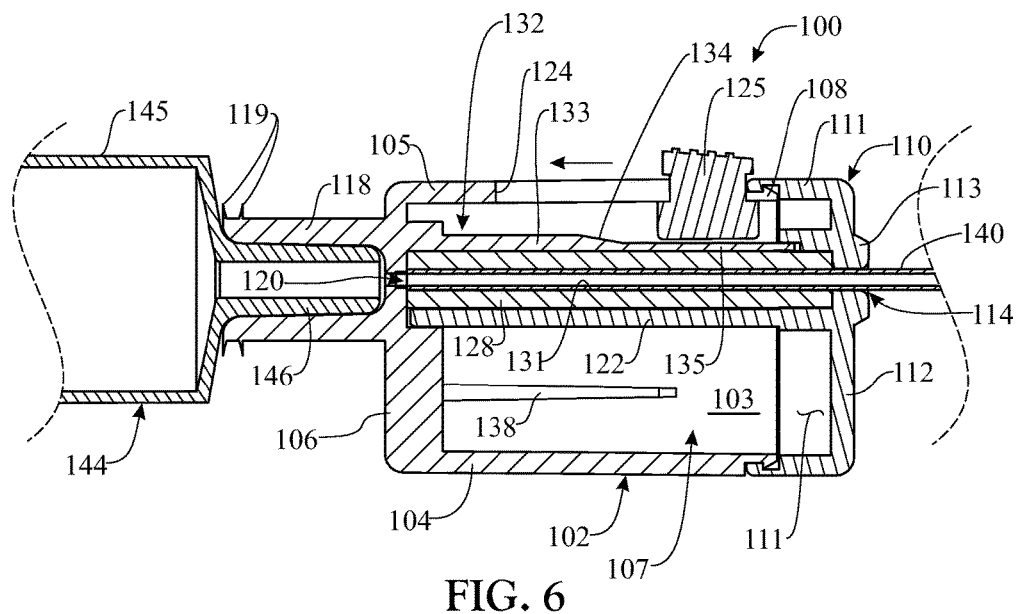
FIG. 6 is a cross-sectional side elevation view of the catheter connector device with the catheter and the syringe attached to the device, taken along the same sectional plane as FIG. 4, more particularly illustrating a slide button or switch on the device in an unlocking position.
Figure 7:
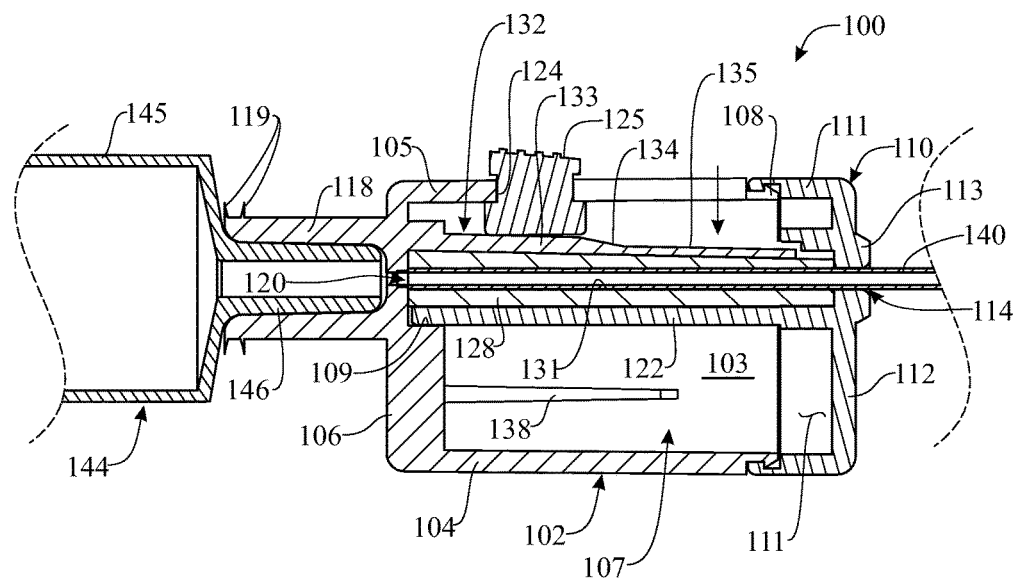
FIG. 7 is a cross-sectional side elevation view of the catheter connector device with the catheter and the syringe attached to the device, taken along the same sectional plane as FIG. 4, more particularly illustrating the switch on the device in a locking position.

As further illustrated in FIGS. 3 and 4, an elongated switch slot 124 extends through the housing top wall 105 of the first housing portion 102. A slide button or catheter lock switch 125 is slidably mounted in and retained within the switch slot 124. The catheter lock switch 125 is selectively positional in variable longitudinal positions along the switch slot 124. In a first main longitudinal position or catheter-unlocking position, as illustrated in FIG. 6, the catheter lock switch 125 is disposed adjacent to the third portion 135 of the sleeve cover 132, there being a gap between an inner surface 126 of the catheter lock switch 125 and the third portion 135. If the catheter lock switch 125 is pushed sufficiently forward, an inner front edge 127 of the catheter lock switch 125 eventually contacts the tapered covered portion 134. Once the inner front edge 127 meets the tapered covered portion 134, a further forward push force exerted on the catheter lock switch 125 causes the inner front edge 127 to exert a frontward and transversely inward force on the tapered covered portion 134. Because the catheter lock switch 125 is transversely retained within the slot and can only move longitudinally, the frontward and transversely inward force on the tapered covered portion 134 causes the cantilevered sleeve cover 132 to flex inward towards the fixed sleeve support portion 122, allowing the catheter lock switch 125 to further move forward along the tapered covered portion 134. Eventually, the cantilevered tapered covered portion 134 is sufficiently flexed inward to allow the catheter lock switch 125, if continued to be pushed forward, to advance onto the first portion 133. Again, because the catheter lock switch 125 is transversely retained within the slot and can only move longitudinally, once the inner surface 126 of the catheter lock switch 125 engages with the first portion 133, as shown in FIG. 7, the sleeve cover 132 is forced by the catheter lock switch 125 to remain in an inward flexed position or catheter-locking position, in which the fixed sleeve support portion 122 is transversely fixed (specifically, by its resting against seat surface 109) and in which the sleeve cover 132 thus partially crimps the tubular sleeve 128, narrowing the sleeve through bore 131. The cantilevered sleeve cover 132 of the present embodiment is elastically biased to transversely shift back to the position of FIG. 6 in the event that the user slides the catheter lock switch 125 back along the slot to overcome the tapered portion 134 and once more face the third portion 135. In consequence, the catheter connector device 100 can be locked and unlocked repeatedly, by simply sliding the catheter lock switch 125 back and forth along the switch slot 124.

Figure 5:
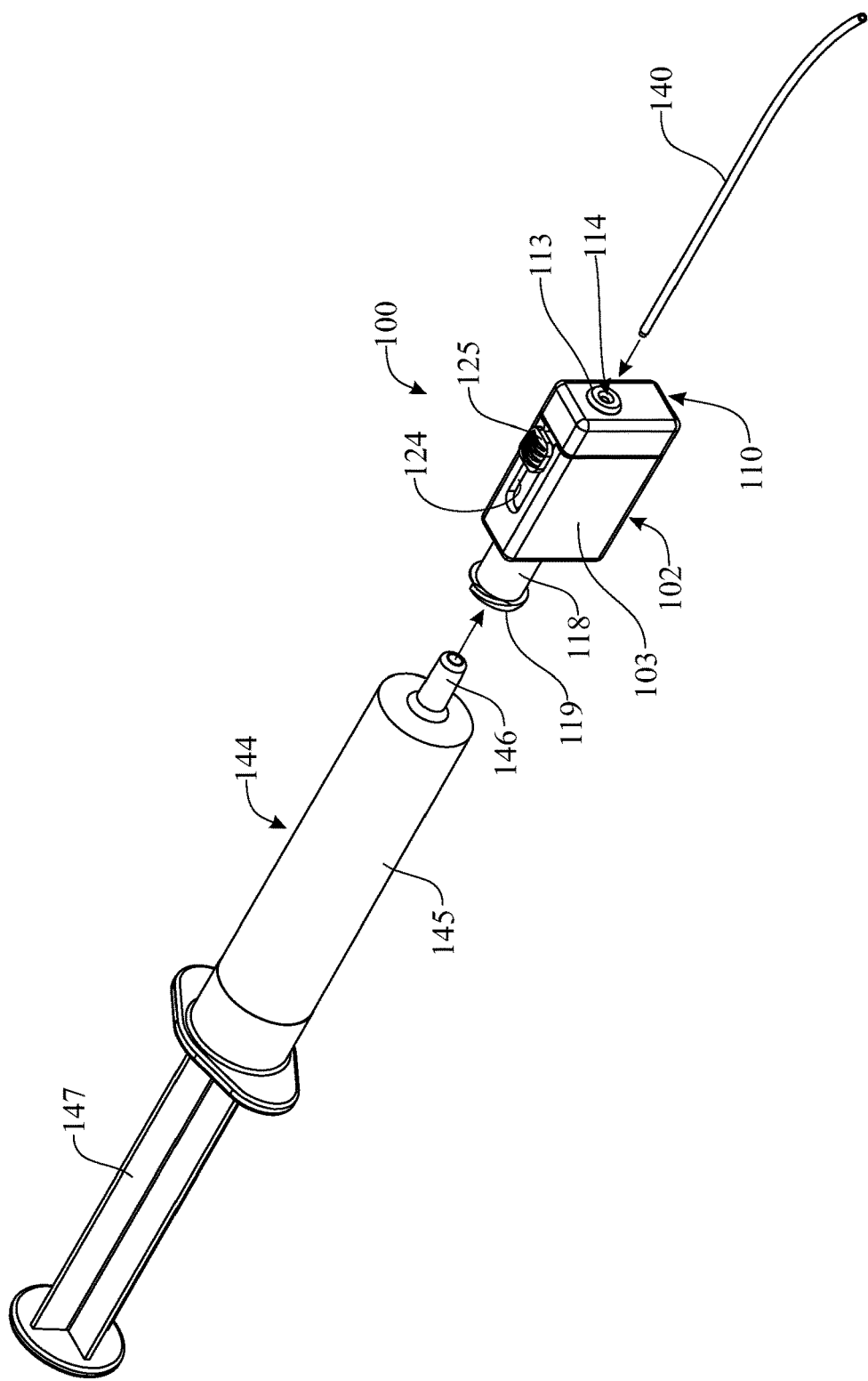
FIG. 5 is an isometric exploded view illustrating typical connection of a catheter and a syringe to the catheter connector device of FIG. 1 in typical application of the device.

Referring next to FIGS. 5 through 7 of the drawings, in typical application, the catheter connector device 100 releasably connects a syringe 144 to an epidural catheter 140 for delivery of epidural anesthetic to a patient (not illustrated). The catheter 140 includes a distal end which is inserted into the epidural space of a patient. The catheter lock switch 125 is deployed in the switch slot 124 to the catheter-unlocking position illustrated in FIG. 6 such that the catheter lock switch 125 disengages the sleeve cover 132 and is disposed adjacent to the third portion 135. As illustrated in FIGS. 6 and 7, a proximal end of the catheter 140 is extended through the second port opening 114 in the second port 113 of the second housing portion 110 and into the sleeve through bore 131 in the tubular sleeve 128. The catheter lock switch 125 may next be displaced from the catheter-unlocking position illustrated in FIG. 6 to the catheter-locking position illustrated in FIG. 7 to engage the first portion 133 of the sleeve cover 132 and crimp the tubular sleeve 128 such that the tubular sleeve 128 crimps and secures the catheter 140 in the sleeve through bore 131 of the tubular sleeve 128.

The syringe 144 or other fluid application and/or removal device is connected to the first port 118 on the first housing portion 102. As shown in FIG. 5, the syringe 144 may have a conventional design with a syringe barrel 145, a syringe nipple 146 extending from the syringe barrel 145 and a syringe plunger 147 deployed in the syringe barrel 145. Accordingly, the syringe barrel nipple 146 may be inserted into the companion first port 118 such that the syringe barrel 145 is disposed in fluid communication with the catheter 140 through the first port opening 120 in the first port wall 106 of the first housing portion 102.

An epidural anesthetic substance can be selectively administered to the patient by pushing the syringe plunger 147 in a conventional manner. The syringe plunger 147 pushes the fluid in the syringe barrel 145 of the syringe 144 through the syringe barrel nipple 146 of the syringe 144 and then through the first port opening 120 of the first port 118 and the catheter 140, respectively, into the patient. Fluids can be selectively removed from the patient by withdrawing the fluids from the patient through the catheter 140, the first port opening 120 of the first port 118 and into the syringe barrel nipple 146 and syringe barrel 145 of the syringe 144, respectively. It will be appreciated by those skilled in the art that the catheter lock switch 125, deployed in the catheter-locking position illustrated in FIG. 7, maintains the catheter 140 in a partially-crimpled yet unobstructed configuration, and allows the physician to securely and yet removably secure the syringe 144 to the catheter 140 during administration and removal of fluids to and from, respectively, the patient. When disconnection of the catheter connector device 100 from the catheter 140 is desired, the catheter lock switch 125 is simply and easily displaced from the catheter-locking position of FIG. 7 to the catheter-unlocking position of FIG. 6 to uncrimp the tubular sleeve 128 and facilitate withdrawal of the catheter 140 from the sleeve through bore 131 of the tubular sleeve 128 and the second port opening 114 of the second port 113, respectively.

Although the catheter connector device 100 is generally disposable, in some embodiments the second housing portion 110 can be selectively detached from the first housing portion 102, as illustrated in FIG. 3, to facilitate cleaning of the housing interior 107, the catheter lock switch 125, the fixed sleeve support portion 122 and the sleeve cover 132 as well as removal and cleaning, maintenance or replacement of the tubular sleeve 128.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A catheter connector device for interfacing between a catheter and a fluid application and/or removal device, comprising:
    a device housing, delimiting a housing interior therein, said device housing comprising a first port and a second port comprising a respective first port opening and second port opening communicating an exterior of said catheter connector device with said housing interior, said device housing further comprising a sidewall having a slot;
    a fixed sleeve support portion extending within the housing;
    a cantilevered flexible sleeve cover extending from the device housing into the housing interior, the cantilevered flexible sleeve cover having a first portion extending from an inside surface of the device housing;
    a flexible tubular sleeve comprising a sleeve through bore, said flexible tubular sleeve being arrangeable in a longitudinal direction within the housing and sandwiched between the fixed sleeve support portion and the cantilevered flexible sleeve cover, with said sleeve through bore in fluid communication with the first and second port openings; and
    a user-operable catheter lock switch, slidable along said slot in said longitudinal direction; wherein
    said catheter connector device is configured to adopt, by selectively sliding said catheter lock switch in opposite directions, a catheter-locking configuration in which an inner surface of the catheter lock switch is slid onto said first portion of the cantilevered flexible sleeve cover and maintains the cantilevered flexible sleeve cover in a flexed position towards the fixed sleeve support portion, compressing the flexible tubular sleeve for gripping a catheter inserted in said through bore of said flexible tubular sleeve, and a catheter-unlocking configuration in which the inner surface of the catheter lock switch does not contact the first portion of the cantilevered flexible sleeve cover and the cantilevered flexible sleeve cover is biased away from the fixed sleeve support portion relaxing said compressing of the flexible tubular sleeve.

2. The catheter connector device of claim 1, wherein said device housing comprises a first housing portion and a second housing portion fastened to one another, wherein said fixed sleeve support portion extends from an inner surface of said second housing portion into said inner space, and wherein said cantilevered flexible sleeve cover extends from an inner surface of said first housing portion.

3. The catheter connector device of claim 1, wherein said catheter connector device is reversibly and repeatedly alterable from said catheter-unlocking configuration to said catheter-locking configuration.

4. The catheter connector device of claim 1, wherein said device housing comprises a first housing portion and a second housing portion fastened to one another, wherein said first port is comprised in said first housing portion and wherein said second port is comprised in said second housing portion.

5. The catheter connector device of claim 4, wherein said fixed sleeve support portion rests transversely on said first housing portion, preventing transverse movement of said fixed sleeve support portion when sliding said catheter lock switch onto said first portion to achieve said catheter-locking configuration.

6. The catheter connector device of claim 1, wherein said first and second ports are arranged at opposite ends of said catheter connector device along the longitudinal direction, and wherein said first port opening, said sleeve bore and said second port opening are aligned along said longitudinal direction.

7. The catheter connector device of claim 6, wherein said slot is arranged in said longitudinal direction.

8. The catheter connector device of claim 1, wherein said cantilevered flexible sleeve cover further comprises a second portion extending from said first portion towards a free end of said cantilevered flexible sleeve cover, said second portion being at a greater distance from said slot than said first portion, and at an increasing distance from said slot.

9. The catheter connector device of claim 8, wherein the second portion is tapered.

10. The catheter connector device of claim 8, wherein said cantilevered flexible sleeve cover further comprises a third portion extending from said second portion towards said free end of said cantilevered flexible sleeve cover, wherein said third portion is at a greater distance from said slot than said first and second portions.

11. The catheter connector device of claim 10, wherein, in said catheter-unlocking configuration, said catheter lock switch is arranged facing said third portion.

12. A catheter connector device for interfacing between a catheter and a fluid application and/or removal device, comprising:
a device housing, delimiting a housing interior therein, said device housing comprising a first port and a second port comprising a respective first port opening and second port opening communicating an exterior of said catheter connector device with said housing interior, said device housing further comprising a sidewall having a slot;
a fixed sleeve support portion extending within the housing;
a cantilevered flexible sleeve cover extending from the device housing into the housing interior, the cantilevered flexible sleeve cover having a first portion extending from an inside surface of the device housing, and a second portion extending from said first portion towards a free end of said cantilevered flexible sleeve cover, said second portion being at a greater distance from said slot than said first portion, and at an increasing distance from said slot;
a flexible tubular sleeve comprising a sleeve through bore, said flexible tubular sleeve being arrangeable in a longitudinal direction within the housing and sandwiched between the fixed sleeve support portion and the cantilevered flexible sleeve cover, with said sleeve through bore in fluid communication with the first and second port openings; and
a user-operable catheter lock switch, slidable along said slot in said longitudinal direction; wherein
said catheter connector device is configured to adopt, by selectively sliding said catheter lock switch in opposite directions, a catheter-locking configuration in which an inner surface of the catheter lock switch is slid onto said first portion of the cantilevered flexible sleeve cover and maintains the cantilevered flexible sleeve cover in a flexed position towards the fixed sleeve support portion, compressing the flexible tubular sleeve for gripping a catheter inserted in said through bore of said flexible tubular sleeve, and a catheter-unlocking configuration in which the inner surface of the catheter lock switch does not contact the first portion of the cantilevered flexible sleeve cover and the cantilevered flexible sleeve cover is biased away from the fixed sleeve support portion relaxing said compressing of the flexible tubular sleeve.

13. The catheter connector device of claim 12, wherein said cantilevered flexible sleeve cover further comprises a third portion extending from said second portion towards said free end of said cantilevered flexible sleeve cover, wherein said third portion is at a greater distance from said slot than said first and second portions.

14. The catheter connector device of claim 13, wherein, in said catheter-unlocking configuration, said catheter lock switch is arranged facing said third portion.

15. The catheter connector device of claim 12, wherein said first and second ports are arranged at opposite ends of said catheter connector device along the longitudinal direction, and wherein said first port opening, said sleeve bore and said second port opening are aligned along said longitudinal direction.

16. The catheter connector device of claim 15, wherein said slot is arranged in said longitudinal direction.

17. A catheter connector device for interfacing between a catheter and a fluid application and/or removal device, comprising:
a device housing, delimiting a housing interior therein, said device housing comprising a first port and a second port comprising a respective first port opening and second port opening communicating an exterior of said catheter connector device with said housing interior, said device housing further comprising a sidewall having a slot;
a fixed sleeve support portion extending within the housing;
a cantilevered flexible sleeve cover extending from the device housing into the housing interior, the cantilevered flexible sleeve cover having a first portion extending from an inside surface of the device housing, a second portion extending from said first portion towards a free end of said cantilevered flexible sleeve cover, said second portion being at a greater distance from said slot than said first portion, and at an increasing distance from said slot, and a third portion extending from said second portion towards said free end of said cantilevered flexible sleeve cover, wherein said third portion is at a greater distance from said slot than said first and second portions;
a flexible tubular sleeve comprising a sleeve through bore, said flexible tubular sleeve being arrangeable in a longitudinal direction within the housing and sandwiched between the fixed sleeve support portion and the cantilevered flexible sleeve cover, with said sleeve through bore in fluid communication with the first and second port openings; and
a user-operable catheter lock switch, slidable along said slot in said longitudinal direction; wherein
said catheter connector device is configured to adopt, by selectively sliding said catheter lock switch in opposite directions, a catheter-locking configuration in which an inner surface of the catheter lock switch is slid onto said first portion of the cantilevered flexible sleeve cover and maintains the cantilevered flexible sleeve cover in a flexed position towards the fixed sleeve support portion, compressing the flexible tubular sleeve for gripping a catheter inserted in said through bore of said flexible tubular sleeve, and a catheter-unlocking configuration in which the inner surface of the catheter lock switch does not contact the first portion of the cantilevered flexible sleeve cover and the cantilevered flexible sleeve cover is biased away from the fixed sleeve support portion relaxing said compressing of the flexible tubular sleeve.

18. The catheter connector device of claim 17, wherein, in said catheter-unlocking configuration, said catheter lock switch is arranged facing said third portion.

19. The catheter connector device of claim 17, wherein said first and second ports are arranged at opposite ends of said catheter connector device along the longitudinal direction, and wherein said first port opening, said sleeve bore and said second port opening are aligned along said longitudinal direction.

20. The catheter connector device of claim 19, wherein said slot is arranged in said longitudinal direction.

* * * * *